(12) United States Patent
Buzzatti et al.

(10) Patent No.: US 12,109,053 B2
(45) Date of Patent: Oct. 8, 2024

(54) DEVICE FOR USE IN DYNAMIC RADIOLOGICAL IMAGE ACQUISITION (71) Applicant: VRIJE UNIVERSITEIT BRUSSEL, Brussels (BE)

(72) Inventors: Luca Buzzatti, Jette (BE); Benyameen Keelson, Evere (BE); Erik Cattrysse, Wuustwezel (BE); Nico Buls, Asse (BE); Gert Van Gompel, Mechelen (BE); Johan De Mey, Dilbeek (BE); Thierry Scheerlinck, Wilrijk (BE); Jef Vandemeulebroucke, Ganshoren (BE); Jean-Pierre Baeyens, Brasschaat (BE); Kevin Langlois, Schaarbeek (BE); Dirk Lefeber, Sint Agatha Rode (BE); Carlos David Rodriguez Guerrero, Elsene (BE)

(73) Assignee: VRIJE UNIVERSITEIT BRUSSEL, Brussels (BE)

( * ) Notice: Subject to any disclaimer, the term of this patent is extended or adjusted under 35 U.S.C. 154(b) by 239 days.

(21) Appl. No.: 17/909,542

(22) PCT Filed: Mar. 2, 2021

(86) PCT No.: PCT/EP2021/055138
§ 371 (c)(1),
(2) Date: Sep. 6, 2022

(87) PCT Pub. No.: WO2021/175827
PCT Pub. Date: Sep. 10, 2021

(65) Prior Publication Data
US 2023/0117250 A1 Apr. 20, 2023

(30) Foreign Application Priority Data

Mar. 6, 2020 (EP) .................................... 20161501

(51) Int. Cl.
A61B 6/04 (2006.01)
A61B 6/00 (2006.01)
(Continued)

(52) U.S. Cl.
CPC .......... *A61B 6/0407* (2013.01); *A61B 6/4411* (2013.01); *A61B 6/486* (2013.01); *A61B 6/50* (2013.01); *A61B 6/035* (2013.01)

(58) Field of Classification Search
CPC ...... A61B 6/0407; A61B 6/4411; A61B 6/486
See application file for complete search history.

(56) References Cited

U.S. PATENT DOCUMENTS

| 6,708,693 | B1 | 3/2004 | Choy et al. |
| 2014/0094721 | A1 | 4/2014 | Diallo |
| 2017/0360327 | A1* | 12/2017 | Maher .................... A61B 5/702 |

FOREIGN PATENT DOCUMENTS

| WO | 0145564 A1 | 6/2001 |
| WO | 2017205411 A1 | 11/2017 |

OTHER PUBLICATIONS

International Search Report from PCT Application No. PCT/EP2021/055138, Jun. 4, 2021.

(Continued)

*Primary Examiner* — Hugh Maupin
(74) *Attorney, Agent, or Firm* — Workman Nydegger (57) ABSTRACT A device for use with a four-dimensional radiological imaging modality includes: a base structure and a table slidably mounted with respect to one another. The base structure is at one end provided with a platform at an angle relative to the table, and a counteracting structure is arranged to apply to the table a load exerting force in a direction towards the one end provided with the platform from the opposite end of the base structure or vice versa.

16 Claims, 6 Drawing Sheets (51) Int. Cl.
  *A61B 6/50*    (2024.01)
  *A61B 6/03*    (2006.01)

(56) References Cited

OTHER PUBLICATIONS

Search Report from corresponding European Application No. 20161501.0, Sep. 30, 2020.

Kimura et al., "Ability of a Novel Foot and Ankle Loading Device to Reproduce Loading Conditions in the Standing Position During Computed Tomography," Journal of Medical Devices, vol. 9, Iss. 4, Dec. 1, 2015, pp. 044506-1-044506-4.

Zhang et al., "An in vivo study of hindfoot 3D kinetics in stage II posterior tibial tendon dysfunction (PTTD) flatfoot based on weight-bearing CT scan," Foot & Ankle, Bone & Joint Research, vol. 2, No. 12, Dec. 1, 2013, pp. 255-263.

Williams et al., "The Relationship Between Tibial Tuberosity-Trochlear Groove Distance and Abnormal Patellar Tracking in Patients With Unilateral Patellar Instability," Arthroscopy: The Journal of Arthroscopic & Related Surgery vol. 32, No. 1, as early as Jan. 1, 2016, pp. 55-61.

Tanaka et al., "Correlation Between Changes in Tibial Tuberosity-Trochlear Groove Distance and Patellar Position During Active Knee Extension on Dynamic Kinematic Computed Tomographic Imaging," Arthroscopy: The Journal of Arthroscopic & Related Surgery, vol. 31, No. 9, Sep. 1, 2015, pp. 1748-1755.

Hirschmann et al., "Upright CT of the knee: the effect of weight-bearing on joint alignment," European Radiology, vol. 25, No. 11, May 1, 2015, 8 pages.

* cited by examiner

DEVICE FOR USE IN DYNAMIC RADIOLOGICAL IMAGE ACQUISITION

FIELD OF THE INVENTION

The present invention is generally related to the field of devices that can be used in medical care. More in particular, it relates to devices for creating a weight-bearing condition in medical images like musculoskeletal medical images.

BACKGROUND OF THE INVENTION

Four-dimensional computed tomography (4DCT), also referred to as dynamic CT, is a type of CT scanning which records multiple image data sets over time. It allows playback of the scan as a video, so that physiological processes can be observed and internal movement can be tracked. The name is derived from the addition of time (as the fourth dimension) to traditional 3D computed tomography.

Dynamic CT is an upcoming technique to examine intra-articular and extra-articular pathologies as it provides excellent spatial and temporal resolution of bone motion. One of its main limitations with respect to lower limb acquisition is the fact that it is performed with the patient in a horizontal position and therefore in a non-weight bearing setting.

An example of such a set-up with the patient in horizontal position is found in the paper "*Ability of novel foot and ankle loading device to reproduce loading conditions in the standing position during Computed Tomography*" (T. Kimura et al., Journal of Medical Devices, Vol. 9, Issue 4, 2015, 4 pages). The proposed loading device comprises a foot plate, a backboard and shoulder pads mounted on the backboard so that the shoulders support the load applied to the foot soles. An L-shaped foot plate is employed to apply an axial load to the soles in the cephalic direction. A rope capable of withstanding loads up to 1000 kg is threaded through holes on the foot plate, then through a pulley mounted to the backboard in the cephalic direction and left to hang towards the side of the platform of the CT scanner. Weight plates are hung from a hook attached to the end of the rope to reproduce loading conditions. The loading device of Kimura, however, does not allow movement of the legs: it only provides weight bearing. So, it acquires images in a static position and does not allow acquiring real time dynamic CT data of the moving anatomy.

Also in the paper "*An in vivo study of hindfoot 3D kinetics in stage II posterior tibial tendon dysfunction (PTTD) flatfoot based on weight-bearing CT scan*" (Y. Zhang et al., Bone & Joint Research, vol. 2, no. 12, Dec. 2013, pp. 255-263) a custom made foot-loading device is presented to simulate normal full-body-weight-bearing using a counterbalance. The device comprises two main components: a foot plate with stress sensor and a main frame including a loading control component. A subject is positioned on the scanner bed in a supine position, with the right lower leg fixed to the supporting platform to keep it in a neutral position. The right foot sole is placed on a customised foot plate made of radiolucent materials. The foot plate is L-shaped and slides on the front edges of the main frame base. An external load (such as standard weights or sandbags) is applied to the foot plate through a system of wires and pulleys to simulate physical full-body-weight-bearing with the lower limb muscles under load. Again, this loading device does not allow movement of the legs. In addition, the device contains ferromagnetic materials which prevents its use in any imaging technique which uses magnetic properties, such as Magnetic Resonance Imaging (MRI).

There are cone-beam CTs that allow scanning the patient in orthostatic position (standing), see e.g. "*Upright CT of the knee: the effect of weight-bearing on joint alignment*" (Hirschmann et al., European Radiology (2015) 25:3398-3404). Such a standing CT scanner, however, cannot be used either, as it does not allow acquiring real time joint motion. Rather, it acquires static frames of the knee/ankle/etc in various discrete positions.

Some studies have investigated some aspect of the kinematics of the lower limb using four-dimensional computed tomography. For example, a study on the knee is presented in the papers "*The relationship between tibial tuberosity-trochlear groove distance and abnormal patellar tracking in patients with unilateral patellar instability*" (E. Williams et al., Arthrosc—J Arthrosc Relat Surg, 2016; 32(1):55-61, available from: http://dx.doi.org/10.1016/j.arthro.2015.06.037) and "*Correlation between Changes in Tibial Tuberosity-Trochlear Groove Distance and Patellar Position during Active Knee Extension on Dynamic Kinematic Computed Tomographic Imaging*" (Tanaka et al., Arthrosc-J Arthrosc Relat Surg,. 2015; 31(9):1748-55, from: http://dx.doi.org/10.1016/j.arthro.2015.03.015). However, although these studies apply 4DCT, they perform the movement in a non-weight-bearing condition of the lower limb.

When the lower limb is put under load during the physio (patho)logical movement, this may provide a better insight in the patient's pathology. However, in order to do so there is a need for a device able to provide load during a dynamic movement of the lower limb.

SUMMARY OF THE INVENTION

It is an object of embodiments of the present invention to provide for a device that can create loading conditions of the lower limb when performing dynamic movement while acquiring dynamic radiological images.

The above objective is accomplished by the solution according to the present invention.

In a first aspect the invention relates to a device for use with a four-dimensional radiological imaging modality. The device comprises a base structure and a table slidably mounted with respect to each other. The base structure is at one end provided with a platform at an angle relative to the table. The device further comprises a counteracting structure arranged to apply to the table a load exerting force in a direction towards said one end provided with the platform from the opposite end of the base structure or vice versa.

The proposed solution indeed allows for creating a load condition on the lower limb. A patient lays down with the back on the table and the feet on the platform. When a load is applied, the table moves towards the platform (or, alternatively, the platform of base structure moves with respect to the table) and the patient bends the knees. The applied load exerts a force towards the end of the base structure that lays closest to the patient's feet. The patient tries to resist to the applied force by pushing with both feet against the platform. The patient takes a position as if he were squatting. The device is preferably used with a musculoskeletal four-dimensional radiological imaging modality. The dynamic radiological images are acquired in real time while the patient performs flexion-extension movements at the ankles, knees and hips. This allows studying real-time motion internal structures and tissues, which may include, but are not limited to, bony structures, soft tissues (e.g. muscles, ligaments and tendons), vascular and nervous structures or organs.

In preferred embodiments the base structure and the table are made in a radiolucent and/or non-ferromagnetic material. In this way image artefacts are avoided when acquiring the radiological images on any type of imaging modality. As such, it can be used with CT scanners, magnetic resonance imaging (MRI) scanners, positron emission tomography scanners in combination with CT (PET-CT), single photon emission computed tomography scanners in combination with CT (SPECT-CT), ultrasound imaging and any other type of X-ray imaging, e.g. 2D fluoroscopy imaging.

In embodiments the table is provided with adjustable shoulder supporting means. The shoulder supports protect the patient's shoulders while pushing against the platform to resist the load.

In embodiments of the invention the counteracting structure is movable.

In a preferred embodiment the counteracting structure is implemented with counterweights. The counteracting structure may then comprise a plurality of wheels that each are provided with a floor lock, so that a stable fixation to the floor can be achieved.

In another embodiment the counteracting structure is actuator-driven, e.g. motor-driven.

Advantageously, the device comprises stopping means at the end opposite the end provided with the platform for stopping movement of the table in a direction away from the platform.

In embodiments of the device according to the invention further stopping means are provided to keep the base structure in a fixed position with respect to the counteracting structure. In certain embodiments the further stopping means are a part of the counteracting structure.

In a preferred embodiment the device comprises a lock to keep the table in a fixed position with respect to the base structure. This increases safety when the patient is positioned on the table.

In embodiments the device comprises a removable part to be put on the table in front of the platform, whereby the removable part is so dimensioned as to form an angle of substantially 90° relative to the table.

In some embodiments the angle relative to the table is adjustable.

In another aspect the invention relates to a method for acquiring four-dimensional radiological images of the lower limb of a patient, using a device as previously described. The method comprises:
positioning the device's base structure with the table mounted thereon, on a scanner table,
positioning a patient with the feet on the platform of the base structure and with the lower limb inside a scan field of view of a radiology scanner,
applying a load to the table of the device, said load being related to the patient's weight and exerting force in a direction towards the one end provided with the platform from the opposite end of the base or vice versa,
acquiring the four-dimensional radiological images of the lower limb, while the patient performs a movement to counter the force exerted by the load.

In a preferred embodiment the movement is a cyclic movement of flexion and extension of the patient's ankle, knees and hips. The cyclic movement can be started and ended in any position between full extension and flexion.

In an embodiment the method comprises securing the table mounted on the base structure to the scanner table.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiment(s) described hereinafter.

BRIEF DESCRIPTION OF THE DRAWINGS

The invention will now be described further, by way of example, with reference to the accompanying drawings, wherein like reference numerals refer to like elements in the various figures.

DETAILED DESCRIPTION OF ILLUSTRATIVE EMBODIMENTS

The present invention will be described with respect to particular embodiments and with reference to certain drawings but the invention is not limited thereto but only by the claims.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

It should be noted that the use of particular terminology when describing certain features or aspects of the invention should not be taken to imply that the terminology is being re-defined herein to be restricted to include any specific characteristics of the features or aspects of the invention with which that terminology is associated.

In the description provided herein, numerous specific details are set forth. However, it is understood that embodiments of the invention may be practiced without these specific details. In other instances, well-known methods, structures and techniques have not been shown in detail in order not to obscure an understanding of this description.

Dynamic computed tomography (CT), also referred to as four-dimensional CT (4DCT), is a relatively new domain. Only recently it has been considered for studying the musculoskeletal system.

The present invention proposes in one aspect a device which allows examining a patient's lower limb in a dynamic weight-bearing condition during image acquisition by a real-time dynamic CT scan. The device offers the possibility to properly load the leg during dynamic movement while performing a real-time dynamic CT scan. In this way new options for investigating a patient's lower limb are created. Use of the proposed device allows for close kinetic chain movement. The segment more distant from the body, in this case the foot, is fixed to an immovable object (i.e. a platform) while the more proximal segments are allowed to move under load. Movement of any joint in the kinetic chain causes a kinematic adjustment of the other joints. From a strict engineering perspective, the chain is "closed" if both ends are fixed to a common object, much like a closed circuit. Close kinetic chain movement is the closest condition of a physiological day-to-day activity movement like a squat.

Figure 1:
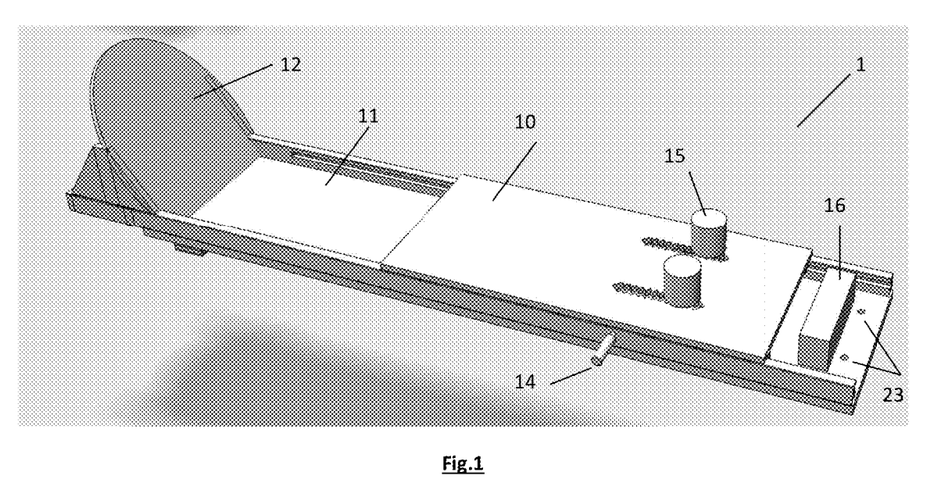
FIG. 1 illustrates an embodiment of the table and base structure with platform of the device according to the present invention.

An illustration of an embodiment of the device according to the invention is provided in FIG. 1. The device (1) comprises a table (10), also referred to as bed in this description, mounted on a fixed base structure (11). The table can slide over the base structure. The base structure is at one end provided with a platform (12) making an angle relative to the table. The device (1) further comprises a counteracting structure (not shown in FIG. 1) to apply a load to the table.

The device is intended to be put on top of a scanner table. When implementing the device, only radiolucent and/or non-ferromagnetic material is used for components, so that the artefacts in the acquired medical images can be avoided. In preferred embodiments the device is nearly entirely made of wood. The various wooden parts may be glued together in certain embodiments. In certain embodiments some parts that remain outside the field of view may be screwed together for a better fixation. In parts of the device that never enter the scan field of view, non-radiolucent materials can be used. Further, the table and the base structure of the device have dimensions that match with the shape, e.g. concave shape, of the table. The base structure with the table on it is designed to avoid any physical contact with the sides of the scanner device.

Figure 2:
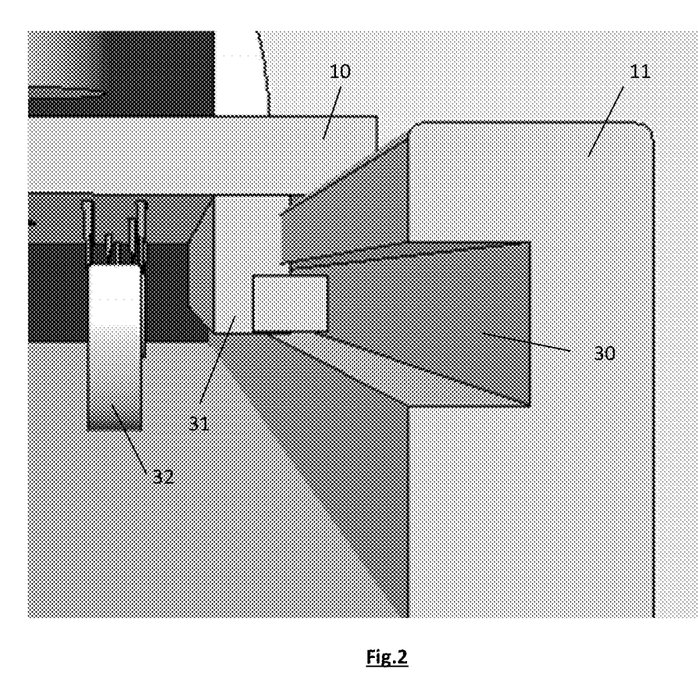
FIG. 2 illustrates an embodiment of the device wherein the base structure has lateral grooves and the table is provided with wheels.

In preferred embodiments the fixed based structure comprises two lateral rails or grooves (30) which can receive a fitting extension (31) of the bed. Reference is made to FIG. 2. Wheels (32) are provided underneath the bed to allow movement over the bottom of the base structure. As such, the bed can slide along the base structure in a single longitudinal direction.

The bed is in preferred embodiments covered with a cover pillow, e.g. made of foam. The cover itself may be in a washable material. The cover pillow may be removable.

Advantageously securing means are provided to keep the patient in position on the table while the device is in use. In a preferred embodiment, as shown in FIG. 1, the securing means are shoulder supports (15) on the upper side of the bed. As such, the patient can exert a pushing force with the feet on the platform to resist the load without sliding on the bed. The shoulder supports are adjustable in position, so that their position can be adapted to the size of the patient lying on the bed. Further also the distance between the two supports can be adjusted. The shoulder supports are preferably made of a sanitary material that is washable. An alternative embodiment uses one or more belts, e.g. around the shoulders, instead of shoulder supports. The belts may be wound around the table (10).

The base structure can be secured to the scanner table. The base structure comprises a number of fixation holes (23) which can be used for securing.

The sliding table can be locked on the base structure in order to allow a patient to go on the table in a safe way. A lock (14) is provided thereto in certain embodiments, as shown in FIG. 1. At the end opposite the end provided with the platform the table may further be equipped with stopping blocks (16). The stopping blocks (16) limit the range (distance) over which the table can move in a direction away from said platform.

As already mentioned the base structure (11) is at one end provided with a platform (12) on which the patient's feet can be placed. In some embodiments the platform makes a fixed angle with the flat surface of the base structure. In other embodiments the angle is adjustable. This adjusting may be performed manually or electrically, as is well known to the person skilled in the art. The angle can in some embodiments vary in a range between 100° and 140° or between 110° and 130°. Preferably the angle is about 120°. In other embodiments the angle may be substantially 90°.

Figure 3:
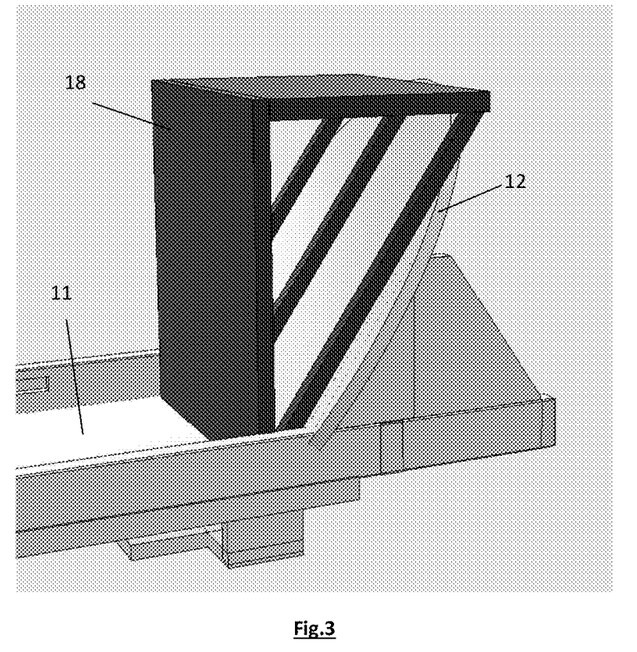
FIG. 3 illustrates the use of a removable part to create an angle of 90° with the surface of the base structure.

In an advantageous embodiment the device further comprises a removable part (18) to be put on the table in front of the platform, as illustrated in FIG. 3. The removable part is so dimensioned that when placed in front of the platform, a resulting angle of 90° relative to the table is obtained. Using this removable part allows investigating a situation as if the patient were standing on the ground.

The device of the invention further comprises a counteracting structure to apply a load to the table.

In a preferred embodiment the counteracting structure is a counter-weight structure. The counterweight structure is positioned at the same side with respect to the table as the platform. The counter-weight structure is provided with one or, typically, more pulleys. A cable or a rope is used to connect the weights. On the other side the cable or rope is attached to the distal end of the table, i.e. the end opposite the end with the platform. In certain embodiments the counter-weight structure may have a parallelepiped shape and be equipped with four wheels and a floor lock that allows lifting the entire structure.

Figure 4:
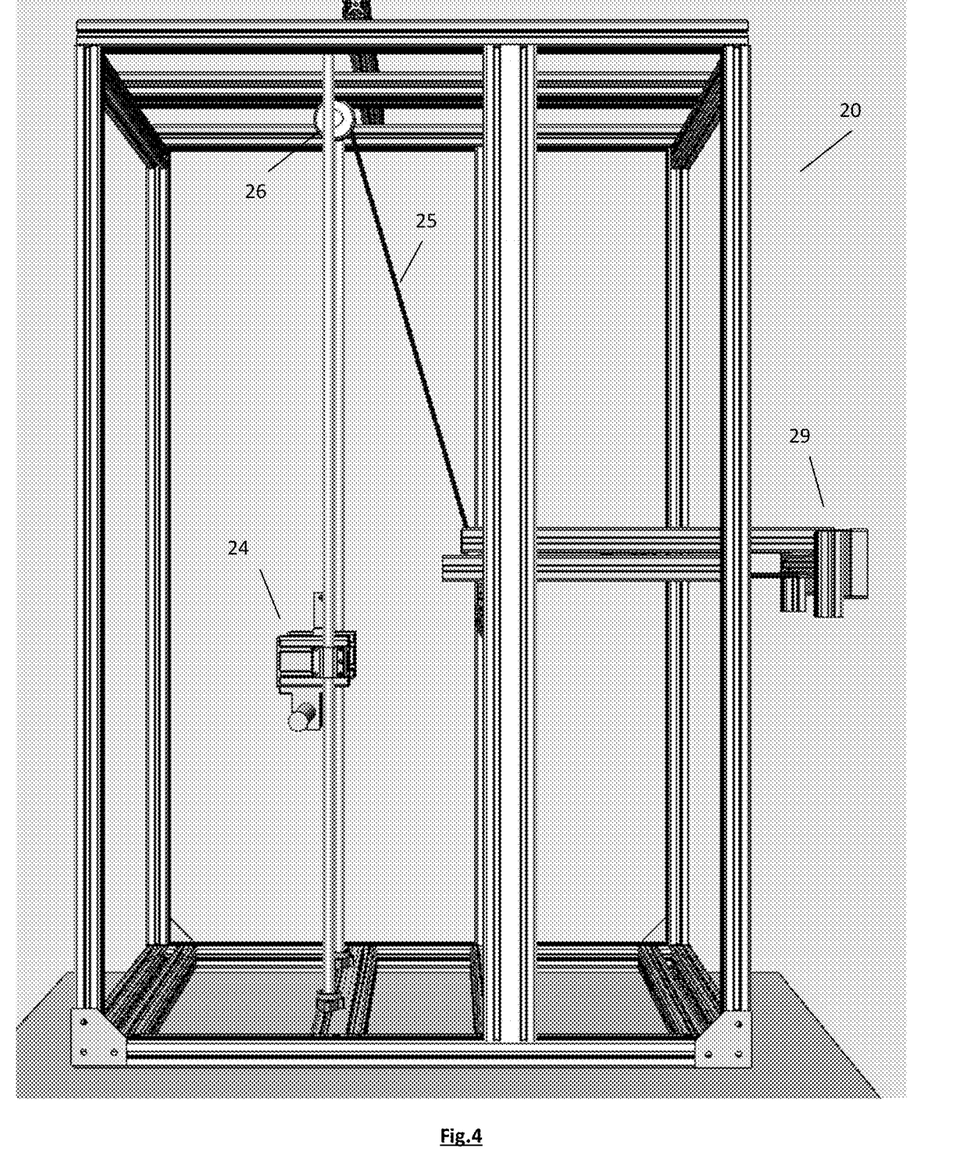
FIG. 4 illustrates an implementation of a counter-weight structure.

FIG. 4 provides an illustration of a possible implementation of the counteracting structure (20) as a counter-weight system. The counter-weight system comprises one or more pulleys (26). The weights (24) are via a cable (25) connected to the table at its end opposite the end with the platform, as already explained previously. For reasons of clarity the platform is not shown in FIG. 4. In the implementation of FIG. 4 the counter-weight system is in direct contact with the floor.

In advantageous embodiments the device is equipped with stopping means (29) to keep the base structure in a fixed position with respect to the counteracting structure. In this way it is avoided that the base structure slides towards the counteracting structure, which might happen because the scanner table often cannot be maintained in a fixed position when a load is applied. In an embodiment as in FIG. 4 the stopping means is a part of the counteracting structure. In other embodiments the stopping means may be a part of the base structure.

Figure 5:
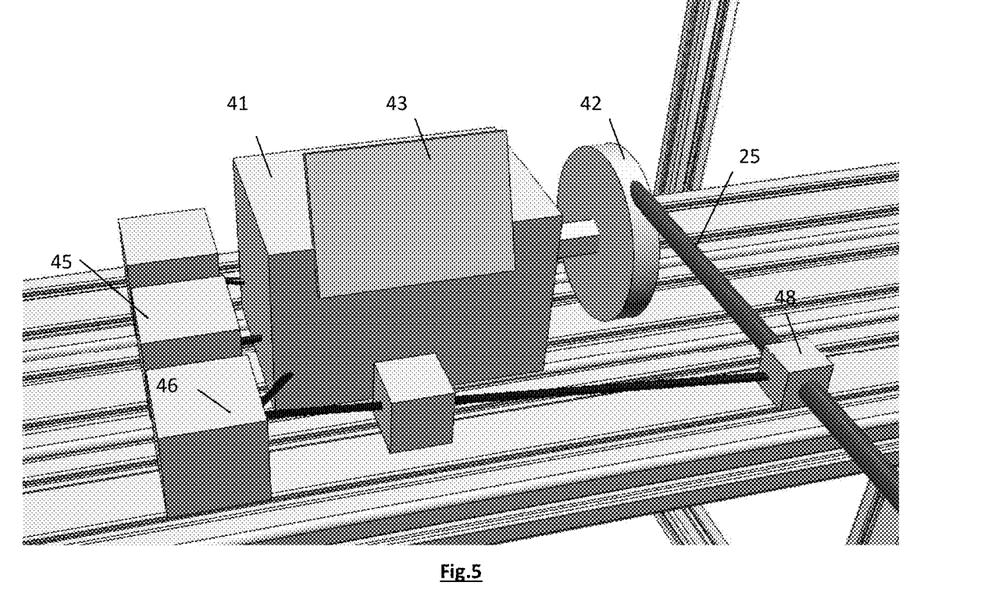
FIG. 5 illustrates an implementation of a motor-driven counter-weight structure.

In another preferred embodiment the counteracting structure is motor driven. The motor can then provide the required load. The counteracting structure can be either mounted on a metal frame or attached at the end of the base structure (11). The latter option makes the entire system more compact as there is no need for the metal frame of the counteracting structure, but the former offers the advantage of a lighter and easier to manage base structure. The motor driven counteracting structure preferably incorporates a user-friendly display that allows setting the desired load. One option may be that information relating to the subject's weight and the body weight percentage is entered to obtain the corresponding load. The generated load always operates in the same direction. When the subject is pushing him/herself away from the platform the motor generates a counteracting load, while when the subject has reached full knees extension the motor generates a force to bring the table (10) back to its original position. In other words, it acts in the same way as the weight that provides a force always in the direction of the counteracting structure. In a possible embodiment, see FIG. 5, a cable (25) is fixed on a wheel (42) connected to a motor (41). The wheel revolves due to the action of the motor in the desired direction, thereby producing the desired torque and therefore desired load. The applied load can be selected using a display (43), e.g. a touch screen. The counteracting structure can be implemented with one or more load cells (48) that allow providing feedback to the motor, through the controller unit (46), and adjusting the torque in real-time. The various functional blocks in FIG. 5 receive power from a power supply (45).

In another embodiment the counteracting structure comprises one or, preferably, more springs or one or, preferably, more rubber bands to provide the required adjustable load.

In another embodiment the table is fixed on the base structure, while the platform is movable. The subject positions himself/herself on the table with the feet on the platform. When the subject pushes against the platform and extends the knees, the platform slides, thanks to sliding means (i.e. rails, one or more wheels, possibly motor driven), away from the subject and when the subject flexes the knees, it comes back in the original position. Therefore, the counteracting structure has to be positioned either on the opposite side of the platform (w.r.t. the scanner) and directly connected with the platform or on the same side of the platform and connected through a pulley to the platform. These two options allow having the load pointing in the direction from the platform towards the subject.

While in the above explanation a device for use in a musculoskeletal four-dimensional computed tomography image acquisition, the invention relates in other aspects to a device suitable for use with any other radiological imaging modalities like e.g. magnetic resonance imaging (MRI), ultrasound, PET-CT, SPECT-CT, fluoroscopy and so on.

Figure 6A:
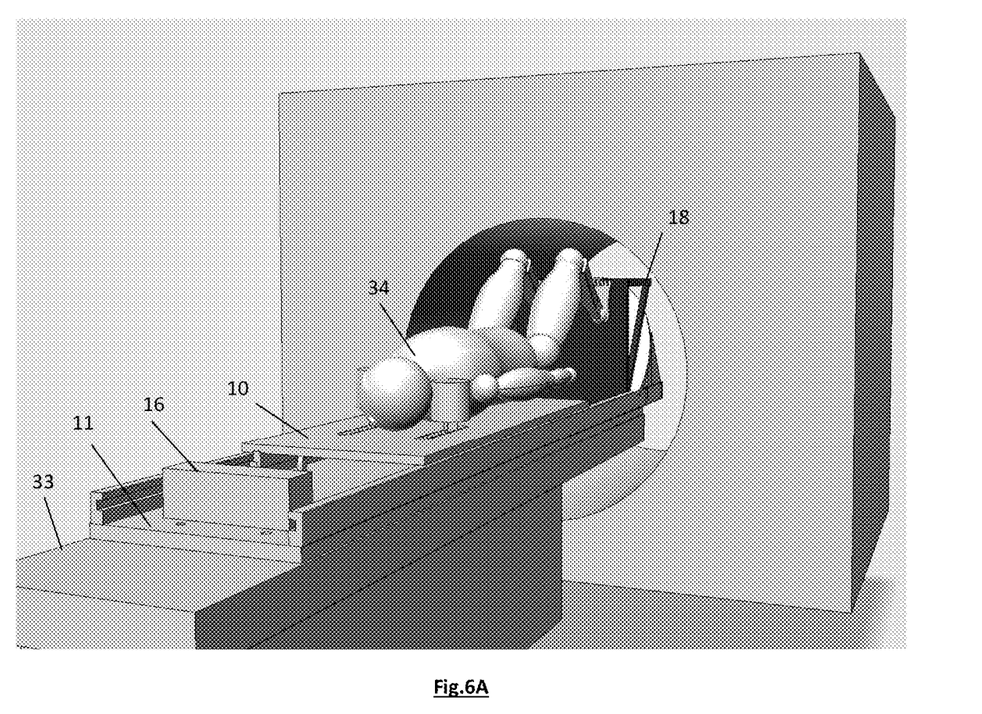
FIGS. 6A and 6B illustrate the use of the device according to the invention.
Figure 6B:
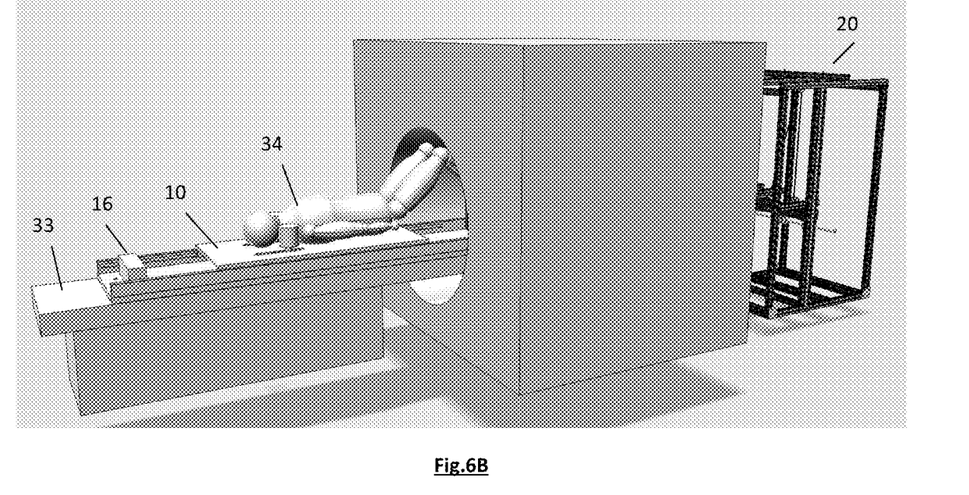

In another aspect the invention relates to a method for acquiring a musculoskeletal four-dimensional radiological image of the lower limb of a patient, wherein a device is used as described above. FIGS. 6A and 6B provide an illustration. The base structure with the table arranged thereon is mounted on and, preferably, secured to the scanner table (33). The patient (34) is placed on the table with the feet on the platform of the base structure. The lower limb is positioned in a field of view of the scanner. Note that in FIG. 6A the removable part (18) is used as well. A load is applied to the table by means of the counteracting structure (e.g. with counterweights or motor-driven). The applied load can be selected and depends on the patient's weight and the goal of the study. The load is such that the table is slid over the base structure in the direction of the platform, whereby the patient's knees bend. The patient exerts a counterforce in order to keep the table as much as possible in its original position by pushing with the feet against the platform. While doing so, the radiological images, e.g. 4DCT images, are acquired to record the movement in real time.

As already mentioned, the device as previously described can readily be adapted to be mounted on an MRI machine. In this case, non-ferromagnetic material must be used for the table, the base structure and the counteracting structure. MRI can either be performed in a weight-bearing static position or during dynamic movement according to the clinical goal. The same procedure as in the previous paragraph is applied.

Figure 7:
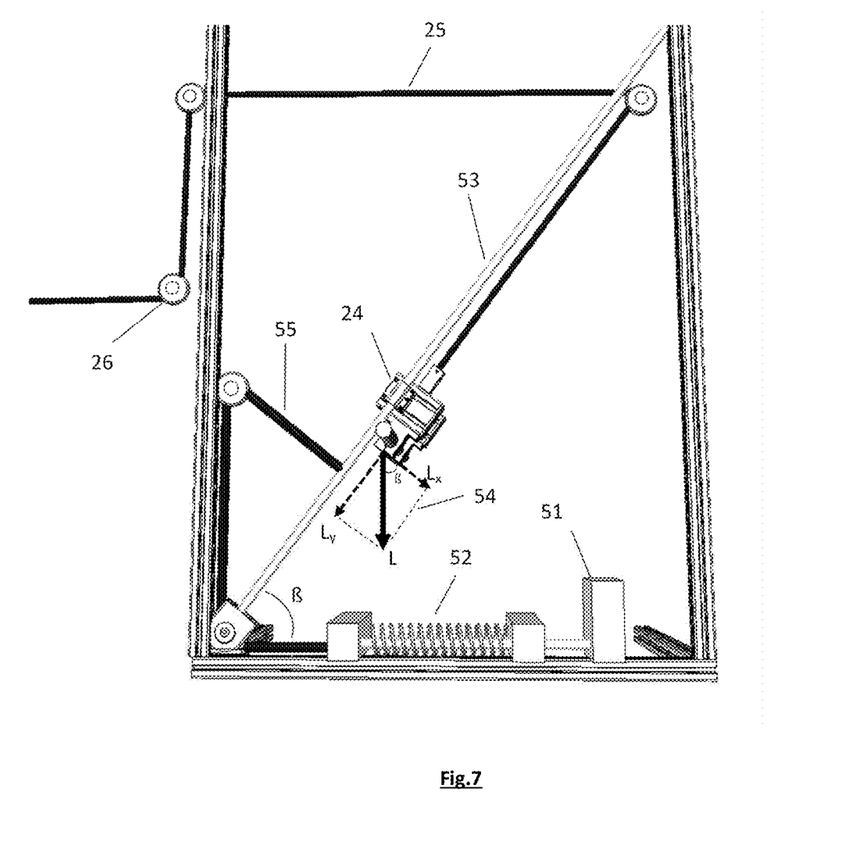
FIG. 7 illustrates another possible implementation of the counteracting structure.

In another embodiment, the counteracting structure can be implemented (see FIG. 7) using a system of springs (52) that through the use of, among other things, one or more cables or belts (55) maintain one or more shafts (53) in equilibrium. Changing the position of the system of springs using an actuator (51) allows changing the angle ß the shafts make with the metal structure. As the load $L_y$ (i.e. the Y component of the load L) (54) transmitted through the cable (26) to the table depends on the angle ß, the load can be adjusted by simply changing the angle ß instead that changing the weights. The actuator control can be linked to, for example, a computer and operated via a graphical user interface.

Figure 8:
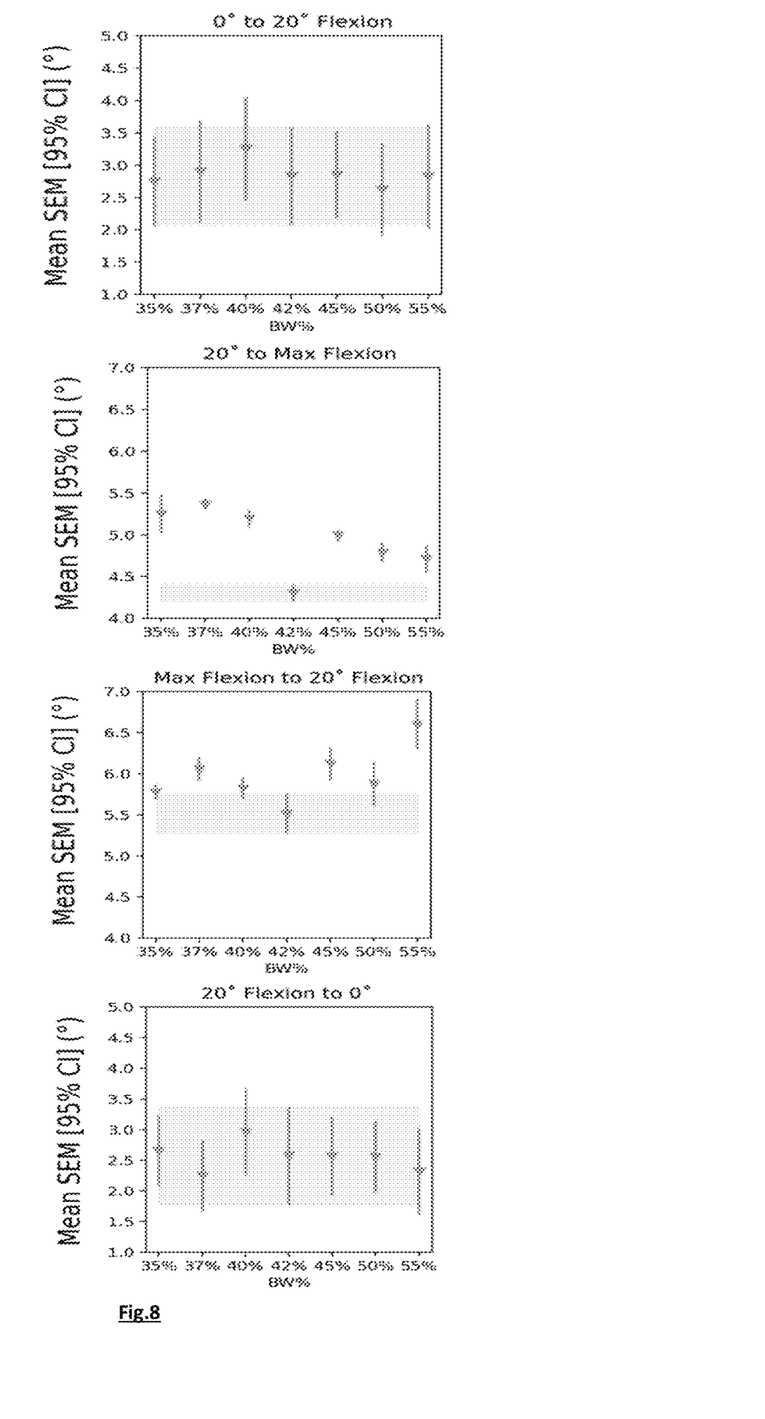
FIG. 8 illustrates SEM (mean and 95% CI) of right and left leg combined for the knee joint.

To validate the device of the invention tests are performed with a number of healthy subjects. The 3D-kinematics is captured with a camera system and muscle activation surface is recorded with surface electromyography (sEMG). The subjects are asked to perform two different tasks: a vertical squat against a door and a horizontal squat on the device. Subjects are allowed to familiarize for few minutes with the two tasks after the subject knee flexion had been standardized. Reflective markers (pelvis, thigh, shank and foot) of the camera system and sEMG sensors (Rectus femoris (RF), Biceps femoris (BF), tibialis anterior (TA) and lateral Gastrocnemius (Ga) of both legs) are positioned. The subjects subsequently perform some repetitions of a vertical squat and of a horizontal squat for a number of sets. Every horizontal squat set has a number of different loading conditions, respectively 35%, 37%, 40%, 42%, 45%, 50% and 55% of the subject's bodyweight (BW %), that are randomized for each subject. To explore the degree of similarity of the left knee's 3D-kinematics, the two conditions are compared using Standard Error of Measurement (SEM) and median differences using the Euclidean Norm of the X, Y, Z axis. EMG activation is expressed as a percentage of maximum voluntary contraction (MVC) and similarity of the different horizontal squats are assessed using mean difference and Intraclass Correlation Coefficient (ICC). Mean SEM of the knee joint shows lowest values for 42% weight in the time interval between 20° of flexion and maximum flexion and between maximum flexion and 20° of the motion cycle, while no differences are seen in the start (0-20°) and end (20-0°) of the motion (FIG. 8). A maximum difference between the two tasks across the entire motion is reported to not be higher than 10°. Mean ICC values of sEMG are shown to be highest for BW % 42, 45 and 37 (Table 1) resulting in an almost excellent reliability (ICC>0.8). Absolute differences between vertical and horizontal squat are smaller for BW % 55, 45 and 42 (Table 2) showing a difference of less than 9% of a MVC.

TABLE 1

ICC Mean difference between vertical and horizontal squat among subjects for sEMG. Right and left leg are combined

| ICC | 35% | 37% | 40% | 42% | 45% | 50% | 55% |
|---|---|---|---|---|---|---|---|
| Rectus Femoris | 0.82 | 0.87 | 0.80 | 0.84 | 0.86 | 0.79 | 0.85 |
| Biceps Femoris | 0.65 | 0.65 | 0.58 | 0.63 | 0.72 | 0.74 | 0.66 |
| Tibialis Anterior | 0.65 | 0.74 | 0.65 | 0.79 | 0.63 | 0.55 | 0.70 |
| Gastrocnemius Lateralis | 0.82 | 0.87 | 0.93 | 0.94 | 0.93 | 0.86 | 0.67 |
| Mean | 0.74 | 0.78 | 0.74 | 0.80 | 0.79 | 0.73 | 0.72 |

TABLE 2

Absolute mean difference between vertical and horizontal squat among subjects. Right and left leg are combined

| | 35% | 37% | 40% | 42% | 45% | 50% | 55% |
|---|---|---|---|---|---|---|---|
| ABS MEAN Rectus Femoris | 13.7 | 12.4 | 12.7 | 11.9 | 11.2 | 12.7 | 9.5 |
| SD | 8.8 | 8.1 | 9.0 | 9.1 | 8.4 | 9.0 | 8.3 |
| ABS MEAN Biceps Femoris | 3.2 | 2.6 | 3.2 | 2.9 | 2.9 | 3.2 | 2.5 |
| SD | 3.7 | 3.5 | 3.3 | 3.7 | 3.0 | 3.3 | 3.6 |
| ABS MEAN Tibialis Anterior | 19.2 | 18.3 | 17.3 | 15.0 | 16.0 | 17.3 | 14.0 |
| SD | 14.8 | 14.7 | 14.8 | 12.8 | 15.1 | 14.8 | 15.5 |
| ABS MEAN Gastrocnemius Lateralis | 7.1 | 6.1 | 4.6 | 5.0 | 4.8 | 4.6 | 7.0 |
| SD | 9.2 | 6.8 | 4.3 | 4.0 | 4.3 | 4.3 | 10.5 |
| ABS Mean TOT | 10.8 | 9.8 | 9.5 | 8.7 | 8.7 | 9.5 | 8.2 |
| SD TOT | 9.125 | 8.275 | 7.85 | 7.4 | 7.7 | 7.85 | 9.475 |

It can be concluded that the proposed device is able to reproduce lower limb kinematics when compared to an orthostatic wall squat.

While the invention has been illustrated and described in detail in the drawings and foregoing description, such illustration and description are to be considered illustrative or exemplary and not restrictive. The foregoing description details certain embodiments of the invention. It will be appreciated, however, that no matter how detailed the foregoing appears in text, the invention may be practiced in many ways. The invention is not limited to the disclosed embodiments.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A device for use with a four-dimensional radiological imaging modality, the device comprising:
   a base structure and a table slidably mounted with respect to one another, said base structure being at one end provided with a platform making an angle relative to said table, and
   a counteracting structure arranged to apply to said table a load exerting force in a direction towards said one end provided with said platform from the opposite end of said base structure or vice versa.

2. The device as in claim 1, wherein said base structure and said table are made in a radiolucent and/or non-ferromagnetic material.

3. The device as in claim 1, wherein said table is provided with adjustable shoulder supporting means.

4. The device as in claim 1, wherein said counteracting structure is movable.

5. The device as in claim 1, wherein said counteracting structure is implemented with counterweights.

6. The device as in claim 5, wherein said counteracting structure comprises a plurality of wheels, each provided with a floor lock.

7. The device as in claim 1, wherein said counteracting structure is actuator-driven.

8. The device as in claim 1, comprising stopping means at the end opposite the end provided with said platform for stopping movement of said table in a direction away from said platform.

9. The device as in claim 1, comprising further stopping means to keep said base structure in a fixed position with respect to said counteracting structure.

10. The device as in claim 9, wherein said further stopping means are a part of said counteracting structure.

11. The device as in claim 1, comprising a lock to keep said table in a fixed position with respect to said base structure.

12. The device as in claim 1, comprising a removable part to be put on said table in front of said platform, said removable part so dimensioned as to form an angle of 90° relative to said table.

13. The device as in claim 1, wherein said angle relative to said table is adjustable.

14. A method for acquiring a four-dimensional radiological image of a lower limb of a patient, using a device as in claim 1, the method comprising:
   positioning said base structure with said table mounted thereon on a scanner table, positioning a patient with the feet on said platform of said base structure and with said lower limb inside a scan field of view of a radiological imaging modality scanner,
   applying a load to said table of said device, said load being related to said patient's weight and exerting force in a direction towards said one end provided with said platform from the opposite end of said base, or vice versa,
   acquiring said four-dimensional image of said lower limb, while said patient performs a movement to counter said force exerted by said load.

15. The method for acquiring as in claim 14, wherein the movement is a cyclic movement of flexion and extension.

16. The method for acquiring as in claim 14, comprising securing the table mounted on the base structure to the scanner table.

* * * * *